United States Patent
Caparso et al.

(10) Patent No.: US 10,493,282 B2
(45) Date of Patent: *Dec. 3, 2019

(54) SYSTEMS AND METHODS FOR DELIVERING NEURAL THERAPY CORRELATED WITH PATIENT STATUS

(71) Applicant: Nevro Corp., Redwood City, CA (US)

(72) Inventors: Anthony V. Caparso, Alexandria, VA (US); Jon Parker, San Jose, CA (US); Andre B. Walker, Monte Sereno, CA (US); Yougandh Chitre, Santa Clara, CA (US)

(73) Assignee: Nevro Corp., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/611,682

(22) Filed: Jun. 1, 2017

(65) Prior Publication Data

US 2018/0104494 A1  Apr. 19, 2018

Related U.S. Application Data

(63) Continuation of application No. 14/944,069, filed on Nov. 17, 2015, now Pat. No. 9,669,219, which is a (Continued)

(51) Int. Cl.
| | | |
|---|---|---|
| A61N 1/36 | (2006.01) | |
| G06F 19/00 | (2018.01) | |

(Continued)

(52) U.S. Cl.
CPC ....... *A61N 1/36139* (2013.01); *A61N 1/3605* (2013.01); *A61N 1/36062* (2017.08);
(Continued)

(58) Field of Classification Search
None
See application file for complete search history.

(56) References Cited

U.S. PATENT DOCUMENTS

| 4,257,429 A | 3/1981 | Dickhudt et al. |
| 4,899,750 A | 2/1990 | Ekwall |

(Continued)

FOREIGN PATENT DOCUMENTS

| JP | 08503648 | 4/1996 |
| JP | 20020527159 | 8/2002 |

(Continued)

OTHER PUBLICATIONS

U.S. Appl. No. 14/161,592, filed Jan. 22, 2014, Thacker et al.
(Continued)

*Primary Examiner* — Kennedy Schaetzle
(74) *Attorney, Agent, or Firm* — Perkins Coie LLP

(57) ABSTRACT

Therapy systems for treating a patient are disclosed. Representative therapy systems include an implantable pulse generator, a signal delivery device electrically coupled to the pulse generator, and a remote control in electrical communication with the implantable pulse generator. The pulse generator can have a computer-readable medium containing instructions for performing a process that comprises collecting the patient status and stimulation parameter; analyzing the collected patient status and stimulation parameter; and establishing a preference baseline containing a preferred stimulation parameter corresponding to a particular patient status.

21 Claims, 7 Drawing Sheets

Related U.S. Application Data continuation of application No. 13/740,917, filed on Jan. 14, 2013, now Pat. No. 9,199,083, which is a continuation of application No. 12/703,683, filed on Feb. 10, 2010, now Pat. No. 8,355,797.

(60) Provisional application No. 61/151,464, filed on Feb. 10, 2009, provisional application No. 61/224,032, filed on Jul. 8, 2009.

(51) Int. Cl.
| | | |
|---|---|---|
| G16H 10/60 | (2018.01) | |
| G16H 20/40 | (2018.01) | |
| G16H 20/70 | (2018.01) | |
| G16H 40/63 | (2018.01) | |
| A61N 1/02 | (2006.01) | |
| A61N 1/372 | (2006.01) | |

(52) U.S. Cl.
CPC ..... *A61N 1/36071* (2013.01); *A61N 1/36132* (2013.01); *G06F 19/3418* (2013.01); *G06F 19/3481* (2013.01); *G16H 10/60* (2018.01); *G16H 20/40* (2018.01); *G16H 20/70* (2018.01); *G16H 40/63* (2018.01); *A61N 1/025* (2013.01); *A61N 1/37235* (2013.01)

(56) References Cited

U.S. PATENT DOCUMENTS

| | | | |
|---|---|---|---|
| 5,016,635 | A | 5/1991 | Graupe |
| 5,031,618 | A | 7/1991 | Mullett |
| 5,224,475 | A | 7/1993 | Berg et al. |
| 5,643,330 | A | 7/1997 | Holsheimer et al. |
| 5,782,884 | A | 7/1998 | Stotts et al. |
| 6,052,624 | A | 4/2000 | Mann |
| 6,155,267 | A | 12/2000 | Nelson |
| 6,236,892 | B1 | 5/2001 | Feler |
| 6,308,102 | B1 | 10/2001 | Sieracki et al. |
| 6,319,241 | B1 | 11/2001 | King et al. |
| 6,353,762 | B1 | 3/2002 | Baudino et al. |
| 6,393,325 | B1 | 5/2002 | Mann et al. |
| 6,440,090 | B1 | 8/2002 | Schallhorn |
| 6,461,357 | B1 | 10/2002 | Sharkey et al. |
| 6,574,507 | B1 | 6/2003 | Bonnet |
| 6,622,048 | B1 | 9/2003 | Mann |
| 6,659,968 | B1 | 12/2003 | McClure |
| 6,740,072 | B2 | 5/2004 | Starkweather et al. |
| 6,895,280 | B2 | 5/2005 | Meadows et al. |
| 6,909,917 | B2 | 6/2005 | Woods et al. |
| 7,024,246 | B2 | 4/2006 | Acosta et al. |
| 7,123,967 | B2 | 10/2006 | Weinberg |
| 7,142,923 | B2 | 11/2006 | North et al. |
| 7,174,215 | B2 | 2/2007 | Bradley |
| 7,289,851 | B2 | 10/2007 | Gunderson et al. |
| 7,317,948 | B1 | 1/2008 | King et al. |
| 7,406,351 | B2 | 7/2008 | Wesselink |
| 7,414,534 | B1 | 8/2008 | Kroll et al. |
| 7,447,545 | B2 | 11/2008 | Heruth et al. |
| 7,463,927 | B1 | 12/2008 | Chaouat |
| 7,489,970 | B2 | 2/2009 | Lee et al. |
| 7,555,346 | B1 | 6/2009 | Woods et al. |
| 7,617,002 | B2 | 11/2009 | Goetz |
| 7,819,909 | B2 | 10/2010 | Goetz et al. |
| 7,853,322 | B2 | 12/2010 | Bourget et al. |
| 7,872,884 | B2 | 1/2011 | Parramon et al. |
| 7,957,797 | B2 | 6/2011 | Bourget et al. |
| 7,957,809 | B2 | 6/2011 | Bourget et al. |
| 8,016,776 | B2 | 9/2011 | Bourget et al. |
| 8,095,220 | B2 | 1/2012 | Lee et al. |
| 8,116,878 | B1 | 2/2012 | Palmer |
| 8,121,703 | B1 | 2/2012 | Palmer |
| 8,355,797 | B2 | 1/2013 | Caparso et al. |
| 8,457,759 | B2 | 6/2013 | Parker et al. |
| 8,498,710 | B2 | 7/2013 | Walker et al. |
| 8,626,312 | B2 | 1/2014 | King et al. |
| 8,712,533 | B2 | 4/2014 | Alataris et al. |
| 8,712,535 | B2 | 4/2014 | Walker et al. |
| 9,061,154 | B2 | 6/2015 | Parker et al. |
| 9,295,840 | B1 | 3/2016 | Thacker et al. |
| 9,399,137 | B2 | 7/2016 | Parker et al. |
| 9,517,344 | B1 | 12/2016 | Bradley et al. |
| 9,731,133 | B1 | 8/2017 | Thacker |
| 9,895,538 | B1 | 2/2018 | Thacker et al. |
| 9,937,348 | B1 | 4/2018 | Bradley |
| 2002/0068930 | A1 | 6/2002 | Tasto et al. |
| 2002/0107553 | A1 | 8/2002 | Hill et al. |
| 2003/0135248 | A1 | 7/2003 | Stypulkowski |
| 2004/0015202 | A1 | 1/2004 | Chandler et al. |
| 2004/0116978 | A1 | 6/2004 | Bradley |
| 2004/0199215 | A1* | 10/2004 | Lee ........... A61N 1/36071 607/48 |
| 2004/0215286 | A1 | 10/2004 | Stypulkowski |
| 2005/0060001 | A1 | 3/2005 | Singhal et al. |
| 2005/0060007 | A1 | 3/2005 | Goetz |
| 2005/0209645 | A1 | 9/2005 | Heruth et al. |
| 2006/0195159 | A1 | 8/2006 | Bradley et al. |
| 2006/0247732 | A1 | 11/2006 | Wesselink |
| 2006/0253174 | A1* | 11/2006 | King ........... A61N 1/36185 607/62 |
| 2006/0259079 | A1 | 11/2006 | King et al. |
| 2007/0013758 | A1 | 1/2007 | Lim et al. |
| 2007/0073357 | A1 | 3/2007 | Rooney et al. |
| 2007/0100378 | A1 | 5/2007 | Maschino |
| 2007/0135868 | A1 | 6/2007 | Shi et al. |
| 2007/0150029 | A1 | 6/2007 | Bourget et al. |
| 2007/0156207 | A1 | 7/2007 | Kothandaraman et al. |
| 2007/0179579 | A1 | 8/2007 | Feler et al. |
| 2007/0208394 | A1 | 9/2007 | King et al. |
| 2007/0213789 | A1 | 9/2007 | Nolan et al. |
| 2007/0249968 | A1 | 10/2007 | Miesel et al. |
| 2007/0250121 | A1 | 10/2007 | Miesel et al. |
| 2007/0255118 | A1 | 11/2007 | Miesel et al. |
| 2007/0265681 | A1 | 11/2007 | Gerber et al. |
| 2008/0015657 | A1 | 1/2008 | Haefner |
| 2008/0046036 | A1 | 2/2008 | King et al. |
| 2008/0064980 | A1 | 3/2008 | Lee et al. |
| 2008/0071325 | A1* | 3/2008 | Bradley ........... A61N 1/36071 607/48 |
| 2008/0109050 | A1 | 5/2008 | John |
| 2008/0154340 | A1 | 6/2008 | Goetz et al. |
| 2008/0188909 | A1 | 8/2008 | Bradley |
| 2008/0215118 | A1 | 9/2008 | Goetz et al. |
| 2008/0269843 | A1 | 10/2008 | Gerber et al. |
| 2008/0281381 | A1 | 11/2008 | Gerber et al. |
| 2008/0319511 | A1 | 12/2008 | Pless |
| 2009/0125079 | A1 | 5/2009 | Armstrong et al. |
| 2009/0149917 | A1 | 6/2009 | Whitehurst et al. |
| 2009/0204173 | A1 | 8/2009 | Fang et al. |
| 2009/0264956 | A1 | 10/2009 | Rise et al. |
| 2009/0264957 | A1 | 10/2009 | Giftakis et al. |
| 2009/0264967 | A1 | 10/2009 | Giftakis et al. |
| 2009/0306746 | A1 | 12/2009 | Blischak |
| 2010/0010432 | A1 | 1/2010 | Skelton |
| 2010/0049280 | A1 | 2/2010 | Goetz |
| 2010/0057162 | A1 | 3/2010 | Moffitt et al. |
| 2010/0069993 | A1 | 3/2010 | Greenspan |
| 2010/0121408 | A1 | 5/2010 | Imran et al. |
| 2010/0121409 | A1 | 5/2010 | Kothandaraman et al. |
| 2010/0185256 | A1 | 7/2010 | Hulvershorn |
| 2010/0274314 | A1 | 10/2010 | Alataris et al. |
| 2010/0274317 | A1 | 10/2010 | Parker et al. |
| 2011/0009927 | A1 | 1/2011 | Parker et al. |
| 2011/0040351 | A1 | 2/2011 | Butson et al. |
| 2011/0071593 | A1 | 3/2011 | Parker et al. |
| 2011/0093051 | A1 | 4/2011 | Davis et al. |
| 2011/0184488 | A1 | 7/2011 | De Ridder |
| 2011/0190847 | A1 | 8/2011 | King et al. |
| 2011/0301679 | A1 | 12/2011 | Rezai |
| 2012/0083857 | A1 | 4/2012 | Bradley et al. |
| 2012/0116476 | A1 | 5/2012 | Kothandaraman |
| 2012/0130448 | A1 | 5/2012 | Woods et al. |
| 2012/0172946 | A1 | 7/2012 | Alataris et al. |
| 2012/0253422 | A1 | 10/2012 | Thacker et al. |

(56) References Cited

U.S. PATENT DOCUMENTS

| | | |
|---|---|---|
| 2012/0265268 A1 | 10/2012 | Blum et al. |
| 2012/0265271 A1 | 10/2012 | Goetz |
| 2013/0023950 A1 | 1/2013 | Gauthier |
| 2013/0060302 A1 | 3/2013 | Polefko et al. |
| 2013/0066411 A1 | 3/2013 | Thacker et al. |
| 2013/0116752 A1 | 5/2013 | Parker et al. |
| 2013/0261694 A1 | 10/2013 | Caparso et al. |
| 2013/0310892 A1 | 11/2013 | Parker et al. |
| 2014/0067016 A1 | 3/2014 | Kaula |
| 2014/0081349 A1 | 3/2014 | Lee et al. |
| 2014/0081350 A1 | 3/2014 | Zhu |
| 2014/0330338 A1 | 11/2014 | Walker et al. |
| 2014/0343622 A1 | 11/2014 | Alataris |
| 2015/0151125 A1 | 6/2015 | Zhu et al. |
| 2015/0165209 A1 | 6/2015 | Grandhe et al. |
| 2015/0217113 A1 | 8/2015 | Walker et al. |
| 2015/0321000 A1 | 11/2015 | Rosenbluth |
| 2017/0014627 A1 | 1/2017 | Walker et al. |
| 2017/0036028 A1 | 2/2017 | Parker et al. |
| 2017/0249444 A1* | 8/2017 | John .................. G06F 19/3468 |
| 2018/0008820 A1* | 1/2018 | Goetz ................ A61N 1/36157 |

FOREIGN PATENT DOCUMENTS

| | | |
|---|---|---|
| JP | 2006502811 A | 1/2006 |
| JP | 2006212458 A | 8/2006 |
| JP | 2008526299 A | 7/2008 |
| JP | 2008534168 A | 8/2008 |
| JP | 2009519771 A | 5/2009 |
| WO | WO-2006119046 A1 | 11/2006 |
| WO | WO-2007149018 A1 | 12/2007 |
| WO | WO-2008142402 A1 | 11/2008 |

OTHER PUBLICATIONS

U.S. Appl. No. 15/017,512, filed Feb. 5, 2016, Thacker et al.

European Search Report for European Patent Application No. 14151730.0, Applicant: Nevro Corporation, dated Jul. 9, 2014, 6 pages.

Hayt et al., "Engine Circuit Analysis," McGraw-Hill Book Company, Fourth Edition, 1986, 18 pages.

International Search Report and Written Opinion, International Application No. PCT/US2010/023787, Applicant: Nevro Corporation, European Patent Office, dated Jun. 2, 2010, 16 pages.

Keuchmann C et al., "853 Could Automatic Position Adaptive Stimulation be Useful in Spinal Cord Stimulation," Abstract, Medtronic, Inc., undated, 1 page.

Notice of Opposition to a European Patent for European U.S. Pat. No. 2,043,589, Proprietor of the Patent: Nevro Corporation; Opponent: Boston Scientific Neuromodulation Corporation, Oct. 22, 2014, 32 pages.

Notice of Opposition to a European Patent for European U.S. Pat. No. 2,403,589, Proprietor of the Patent: Nevro Corporation; Opponent: Boston Scientific Neuromodulation Corporation, Oct. 22, 2014, 32 pages.

Notice of Opposition to a European Patent for European U.S. Pat. No. 2,403,589, Proprietor of the Patent: Nevro Corporation, Opponent: Medtronic, Inc., Oct. 13, 2014, 20 pages.

Nevro Response to Notice of Oppositions of Boston Scientific and Medtronic, Inc., for European U.S. Pat. No. 2,403,589, mailed Jun. 1, 2015, 10 pages.

Opponents: Boston Scientific Response to Proprietor's Response to Notice of Opposition for European U.S. Pat. No. 2,403,589, mailed Jun. 27, 2016, 21 pages.

Opponents: Medtronic, Inc., Additional Observations and Submissions in view of the Oral Proceedings for Opposition for European U.S. Pat. No. 2,403,589, mailed Jan. 20, 2017, 29 pages.

Decision and Minutes: Opposition of European U.S. Pat. No. 2,403,589 by Medtronic, Inc., and Boston Scientific, Apr. 20, 2017, 27 pages.

Extended European Search Report for European Patent Application No. 18174295.8, Applicant: Nevro Corporation, dated Dec. 5, 2018, 7 pages.

* cited by examiner

SYSTEMS AND METHODS FOR DELIVERING NEURAL THERAPY CORRELATED WITH PATIENT STATUS

CROSS-REFERENCE TO RELATED APPLICATIONS

The present application is a continuation of U.S. patent application Ser. No. 14/944,069, filed Nov. 17, 2015, which is a continuation of U.S. patent application Ser. No. 13/740,917, filed Jan. 14, 2013, which is a continuation of U.S. patent application Ser. No. 12/703,683, filed Feb. 10, 2010, which claims priority to the following U.S. Provisional Applications, each of which is incorporated herein by reference: 61/151,464, filed Feb. 10, 2009, and 61/224,032, filed Jul. 8, 2009.

TECHNICAL FIELD

The present disclosure relates generally to systems and methods for delivering neural therapy correlated with patient status.

BACKGROUND

Neurological stimulation or modulation systems have been developed to treat pain, movement disorders, functional disorders, spasticity and various other medical conditions. Implantable neurological stimulation systems may include an implantable pulse generator and one or more leads that deliver electrical pulses to neurological or muscle tissue. In many cases, a physician or caregiver may need to set a variety of stimulation parameters or programs for the patient, which may correspond to different postures, activities, or comfort levels that are assumed to be suitable for the patient. Generally, spinal cord stimulators provide the patient with many different stimulation programs, which are initially set up by the physician or caregiver with patient feedback. The initial setup typically occurs immediately after implant. The patient then uses a patient remote control to change between these programs when the patient's posture, activity, or comfort level has changed. However, in many cases, the preset stimulation levels established at implant may not be suitable for the patient due to slight changes in the lead after implant, scar tissue build-up around the lead after implant, or due to changes in pain patterns over time. These changes may require the patient to routinely adjust the stimulation settings, which requires office visits by the patient. Accordingly, there is a need for improved devices and techniques for customizing a patient's stimulation parameters and automatically adjusting stimulation levels for different patient needs.

DETAILED DESCRIPTION

Figure 1:
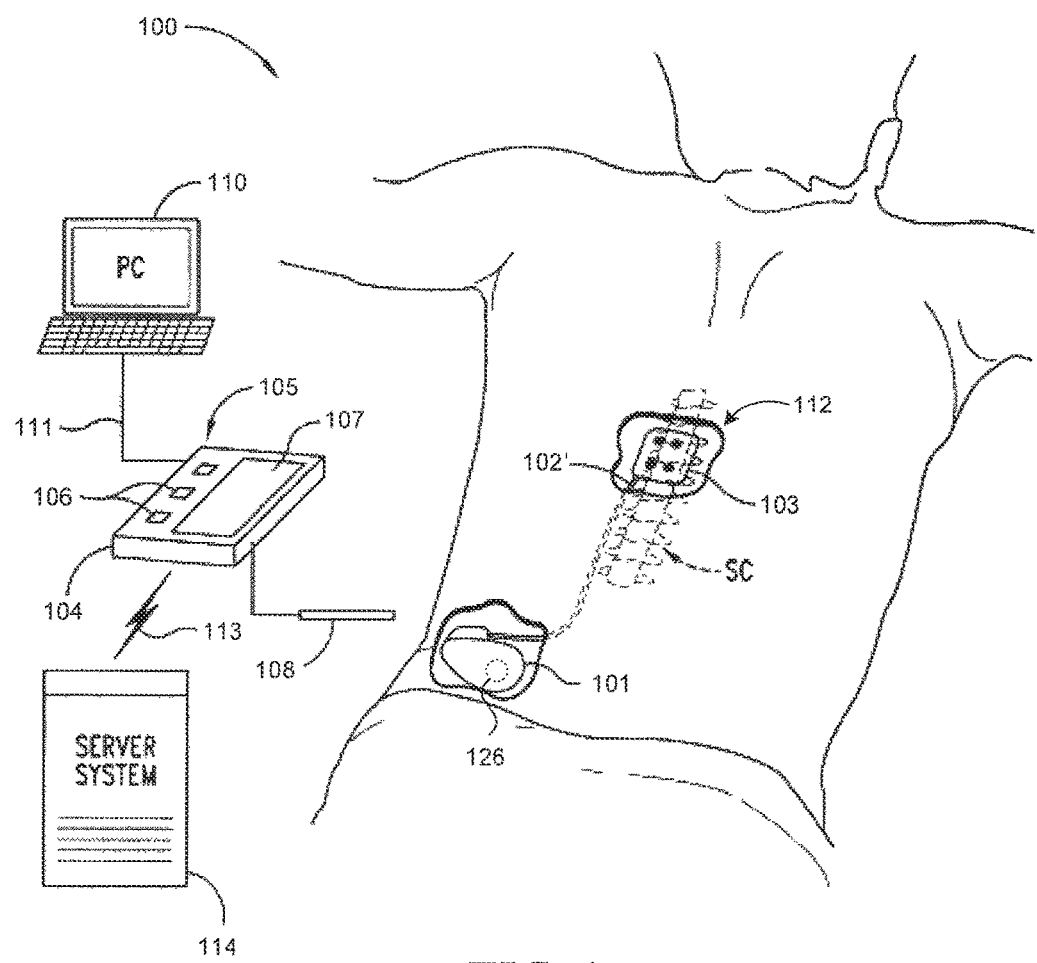
FIG. 1 is a schematic diagram of a therapy system for providing relief from chronic pain to a patient in accordance with embodiments of the present disclosure.

Specific details of several embodiments of this disclosure are described below with reference to implantable spinal cord stimulators for stimulating neural structures, and methods for controllably stimulating a target neural site of a patient. As used herein, the terms "stimulating" and "stimulation" refer generally to signals applied to a patient to elicit a neural response. Unless otherwise specified, the signals may have an inhibitory or facilitatory effect on the target neural population. As used herein, the term "stimulator" applies generally to a device that generates and/or directs stimulation signals. Although selected embodiments are described below with respect to stimulating the dorsal column, dorsal root, dorsal root entry zone and/or other regions of the spinal column to control pain, the implantable stimulators may in some instances be used for stimulating other neurological structures, and/or other tissue (e.g., muscle tissue). Several embodiments can have configurations, components or procedures different than those described in this section, and other embodiments may eliminate particular components or procedures. A person of ordinary skill in the relevant art, therefore, will understand that the invention may have other embodiments with additional elements, and/or may have other embodiments without several of the features shown and described below with reference to FIGS. 1-7C.

Several embodiments of the disclosure are directed to spinal cord stimulation devices (e.g., implantable pulse generators) that have an embedded control algorithm configured to monitor one or more physiological or physical signals from one or more sensors. The sensors can be inside or outside of the implantable device e.g. a spinal cord stimulation device. The sensors can include, for example, an accelerometer, a gyroscope, a blood pressure sensor, an impedance sensor, a thoracic impedance sensor, a heart rate monitor, a respiration rate monitor, a temperature sensor, and/or other suitable sensors. The control algorithm can have two phases—a learning phase and an automatic operation phase, as described in more detail below. In general terms, the control algorithm collects sensor data and correlates it with patient-selected signal delivery data during the learning phase. In the automatic operation phase, the control algorithm receives sensor data and directs the signal delivery based on the correlation established during the learning phase.

In a representative implementation, the spinal cord stimulation device is implanted into a patient. A physician, a device company representative, and/or other authorized personnel can program the spinal cord stimulation device by setting up one or more stimulation programs for the patient and allowing the patient to adjust stimulation parameters including, for example, an amplitude, a pulse width, a frequency, and/or other suitable parameters in the individual programs. Once the programs are established, the patient may have the ability to change only a subset of parameters in an individual program, e.g., only signal amplitude. Also, at the initial setup, the physician or the company representative can initialize the individual sensors with "normal" or expected values. The physician or the company representative can also set a confidence interval for the control algorithm, for example, from about 80% to about 99%, to indicate the end of the learning phase. The physician or the company representative can also set a delta change threshold for the individual sensors, e.g., using 5-10% of the signal average, for detecting abnormal operations of the spinal cord stimulation device and/or sensor inputs that are outside an expected range, as described in more detail below.

During an embodiment of the learning phase, the individual sensors are reset and normalized with initial values, and the spinal cord stimulation device is instructed to start learning by starting the control algorithm. In the learning phase, the spinal cord stimulation device (e.g., via the control algorithm) can continuously monitor the patient for a change of operation. The change of operation can include one or any combination of the following events: (1) a change in a stimulation program, (2) a change in a stimulation parameter, and/or (3) a delta change sensed by any of the sensors. The patient, the physician, or the company representative may cause the stimulation program and/or the parameters to change.

In response to the detected change of operation, the spinal cord stimulation device and/or the control algorithm can record the program settings, sensor readings, and/or other operational parameters associated with the change. For example, the control algorithm can record the time of day, the patient's body position, the patient's activity level, the currently active stimulation program and associated stimulation parameters, and/or other values. In certain embodiments, the sensor readings can be obtained from a gyroscope that senses a posture change, from an accelerometer that measures a change of motion, and/or from an active electrode on a lead body that measures impedance. With the recorded data, the spinal cord stimulation device and/or the control algorithm can build a database to associate the stimulation program and parameter settings with one or more sensor readings.

The database can be populated as the control algorithm learns, by recording the patient inputs. In the learning phase, the patient is in complete control of the spinal cord stimulation device. For example, any time the patient goes to sleep and uses "Program 2" (which has, e.g., a signal frequency of 80 Hz, a pulse width of 150 μsec, and an amplitude of 2.6 mA), the control algorithm populates the database with the time of day (e.g., nighttime), Program 2, and the parameter settings (e.g., frequency, pulse width and amplitude). Over a period of time (e.g., weeks, months, etc.), the spinal cord stimulation device can collect sufficient data to meet the preset confidence intervals and enter the automatic operation phase based on certain sensor readings.

During the automatic operation phase or automatic phase, the stimulation device uses the information in the populated database to set stimulation parameters, given inputs from one or more sensors. For example, the spinal cord stimulation device can enter the automatic phase for at least some body positions (e.g., standing, sitting, laying, etc., as determined by a gyroscope), the gross time of day (e.g., night (sleeping program), morning (active program), evening (watching TV program), etc.), and/or other suitable sensor readings. As a result, when the patient sits down, for example, the spinal cord stimulation device automatically changes the patient stimulation program and/or stimulation parameters to match the patient's preferred values. This change is based on information that the patient entered during the learning phase, rather than on the initial settings entered by the physician or company representative.

The length of time required to meet the confidence intervals may be patient-dependent. Factors that can influence the required amount of time may include the patient's level of use of the device, the number of therapy changes needed, and/or other factors which can vary for each patient depending on the patient's pain and activity level. In several embodiments, once the spinal cord stimulation device has met or exceeded the confidence intervals, the control algorithm enters the automatic phase. Not all conditions must be met before the device can enter the automatic phase. For example, if the spinal cord stimulation device reaches the preset confidence interval for the laying down body position during evening hours, then the spinal cord stimulation device can enter into the automatic phase for these conditions only, without affecting other conditions. The device can continue to operate in the learning phase or mode to collect data for other conditions. In the foregoing examples, identifiers such as "laying down" and "evening" are used for illustrative purposes. In actuality, the system can populate the database with raw and/or modified gyroscope data and clock data, without the need for identifiers.

When the spinal cord stimulation device enters the automatic phase, it can automatically change the stimulation program and/or stimulation parameters for the patient. In certain embodiments, the spinal cord stimulation device can alert the patient before automatically making an adjustment by displaying a message on a patient remote control, by producing a discrete vibration, and/or by utilizing other suitable means. In several embodiments, this alert feature may be removed over time or eliminated entirely.

The spinal cord stimulation device can continuously check for a change of sensor readings, a change in stimulation program, and/or a change in stimulation parameters that are outside the preset delta change thresholds. If such a change is detected and is outside expected limits, in certain embodiments, the spinal cord stimulation device can alert the patient that such a change has occurred. In certain cases, e.g. if the lead impedance is out of range indicating a lead failure or otherwise, the spinal cord stimulation system can notify the physician directly through the central database, by sending an automatic note (e.g. email, fax, voicemail or otherwise as appropriate) of the patient status change. For example, such a change can include a sensor value or a patient-input amplitude that is outside predefined limits, or a requested program change that was not encountered during the learning phase. In response, the patient can override this alert, and the control algorithm can record the event as a new database entry and start to learn more about this new setting, position, stimulation, etc. In other embodiments, the patient can turn off the stimulation therapy and see a physician. The physician can then troubleshoot and plan the next treatment for the patient. The spinal cord stimulation device can reenter the learning mode to learn the new programs, settings, etc. and switch to the automatic phase as described above.

FIG. 1 schematically illustrates a therapy system 100 for providing relief from chronic pain in accordance with embodiments of the present disclosure. The therapy system 100 is shown in FIG. 1 positioned relative to the general anatomy of a spinal cord (labeled "SC" in FIG. 1) of a patient. As shown in FIG. 1, the therapy system 100 can include a pulse generator 101. The pulse generator 101 can be implanted, e.g., subcutaneously, within an abdominal or lower back region of the patient. The pulse generator 101 can be electrically connected to a signal delivery device 112. The signal delivery device 112 can include a lead 102 electrically connected between the pulse generator 101 and an electrode array 103 implanted in close proximity to the spinal cord SC. The signal delivery device 112 can include one or more electrodes or electrode contacts carried by a support substrate. A representative electrode array 103 is disclosed in U.S. patent application Ser. No. 12/104,230, filed Apr. 6, 2008, the disclosure of which is incorporated herein in its entirety by reference. In other embodiments, the signal delivery device 112 can have other configurations. For example, the signal delivery device 112 can include one or more electrodes (e.g., eight electrodes or sixteen electrodes) spaced apart axially and positioned in one or two rows along the lead 102, in place of the electrode array 103.

The pulse generator 101 is configured to generate and transmit stimulation signals to the signal delivery device 112. In certain embodiments, the pulse generator 101 can include a logic processor interconnected with a computer-readable medium containing computer executable instructions, and further connected with input/output devices (e.g., wired or wireless transceivers), power management circuitry, and/or other suitable electrical components (not shown in FIG. 1), as described in more detail below with reference to FIG. 2. The computer-readable medium can include volatile and/or nonvolatile media, e.g., read-only memory (ROM), random access memory (RAM), magnetic disk storage media, optical storage media, flash memory devices, and/or others. In other embodiments, the pulse generator 101 can also include specific hardware components having hard-wired logic (e.g., field-programmable gate arrays) for performing the operations, methods, or processes or with any combination of programmed data processing components and specific hardware components.

In a particular embodiment, the pulse generator 101 includes an embedded sensing element 126 in electrical communication with the logic processor of the pulse generator 101. The sensing element 126 can include at least one of a gyroscope, an accelerometer, a laser sensor, a pressure sensor, a temperature sensor, an impedance sensor, a heart rate monitor, a respiration rate monitor, a clock, and/or other suitable sensors for measuring the current status and/or physiological indicators of the patient. Even though the sensing element 126 is shown in FIG. 1 as integrated into the pulse generator 101, in other embodiments, the sensing element 126 can be positioned remotely from the pulse generator 101 and coupled to the pulse generator 101 with a suitable link (e.g., a wired or wireless link). The system 100 can include a single sensing element 126, or multiple sensing elements 126 depending on factors including patient condition, patient diagnosis, patient preference and/or practitioner preference.

The therapy system 100 can also include a remote control 105 configured to communicate with and/or control the implantable pulse generator 101. As shown in FIG. 1, the remote control 105 includes a housing 104 carrying multiple input devices 106 (e.g., push buttons, track wheels, directional keys, etc.), a display 107 (e.g., a liquid crystal display), and an antenna 108 (e.g., an induction wand). The remote control 105 can also include internal circuitry (not shown) configured to produce a modulated signal and then transmit (via long range telemetry) the modulated signal to the pulse generator 101. In response to the transmitted signal, the pulse generator 101 can, for example, modulate the received signal into a return signal and transmit the modulated return signal carrying requested information to the remote control 105 according to a suitable protocol (e.g., frequency shift key, phase shift key, quad phase shift key, etc), or adjust its operation by changing a stimulation program and/or stimulation parameters. In certain embodiments, the remote control 105 is configured as a handheld device. In other embodiments, components of the remote control 105 can have other portable or stationary configurations.

Optionally, in certain embodiments, the therapy system 100 can include a personal computer 110 coupled to the remote control 105 via a communication link 111 (e.g., a USB link, an Ethernet link, a Bluetooth link, etc.). In other embodiments, the personal computer 110 can be coupled to a network server 114 via a network connection 113 (e.g., an internet connection, an intranet connection, etc.) In yet other embodiments, the personal computer 110 and/or the network server 114 may be omitted. In further embodiments, the therapy system 100 can also include routers, switches, data storage centers, and/or other suitable network components.

After implanting the pulse generator 101, a caregiver (e.g., a physician or a pulse generator company representative) can first configure the pulse generator 101 with an initial set of operating programs and/or parameters using an external programmer (not shown). The caregiver may first configure the pulse generator 101 with an initial set of operating parameters for different patient status variables, such as for different pain areas or types and different patient body positions, patient physical activity levels, time of day, various physiological indicators of the patient, and/or other suitable patient status variables. The initial set of operating parameters can include frequencies, amplitudes, electrode selections for the signal delivery device 112, and/or other suitable parameters. For example, in one embodiment, the initial set of operating parameters can include a first amplitude for a first body position (e.g., standing) and a second amplitude for a second body position (e.g., lying down). In another embodiment, the initial set of operating parameters can also include a first electrode configuration that relates to a first pain area (e.g. the lower back) and a second electrode configuration that relates to a second pain area (e.g. the left leg). In other embodiments, the initial set of operating parameters can also include other operating parameters based on the time of day, physiological indicators of the patient, and/or other suitable process variables. According to the initial set of operating parameters programmed, the pulse generator 101 can apply therapy signals (e.g., electrical impulses) to the nerve fibers of the patient, such as to up-regulate (e.g., stimulate or facilitate) and/or down-regulate (e.g., block or inhibit) the neural response.

One operational difficulty associated with conventional implementations of the foregoing technique is that the initial set of parameters may not be suitable for the patient outside of a clinical setting. For example, without being bound by theory, it is believed that the signal delivery device 112 may shift when the patient is active (e.g., when the patient runs, walks, and/or engages in other activities) or when the patient changes from one body position to another (e.g., among positions such as standing, sitting, lying down, and/or others). The shifting of the signal delivery device 112 may render the applied therapy signals less effective for relieving pain, and/or may cause patient discomfort. It is also believed that the patient's perception of pain may be different at different activity levels. As a result, the initial set of parameters for the pulse generator 101 may not be effective to achieve and/or maintain treatment efficacy over an extended period of time and/or over the course of the patient's typical activities. The patient does have the option of adjusting the stimulation program and/or parameters with the remote control 105 (e.g., configured as a handheld device), within the preset values done at implant. However, the adjustment process using the remote control 105 may be cumbersome, restrictive, and/or time-consuming.

To overcome the above described operational difficulties, the presently disclosed therapy system 100 can be configured to (1) establish patient selections (e.g., preferences) during an initial period (e.g., a learning period); and (2) subsequently automatically adjust the stimulation parameters based, at least in part, on (a) the patient preferences learned during the initial period and (b) the current status (received through the sensors) of the patient. The patient preferences may include patient-selected or patient-preferred values of suitable stimulation parameters and may be referred to collectively as a preference baseline. Once the patient preferences are established, the pulse generator 101 can automatically adjust the stimulation parameters provided to the electrode array 103 in response to a change in the patient's activity level, body position and/or other variable to improve and/or maintain treatment efficacy, without further input from the patient.

During the initial (learning) period, the pulse generator 101 can continuously monitor the current status of the patient (via the sensing element 126) and/or the operation of the pulse generator 101 for a change. For example, in certain embodiments, the pulse generator 101 can sense a change when the patient changes at least one of a stimulation program (e.g., from a "day" program to a "night" program), a stimulation parameter (e.g., an amplitude and/or a frequency of stimulation), and/or other suitable parameters. In certain embodiments, the patient can request or implement an increase or decrease in the amplitude of the applied therapy signals using the remote control 105, and the pulse generator 101 records the patient's change and/or any adjustments to the amplitude. In other embodiments, the pulse generator 101 can sense a change of operation under other suitable conditions.

When the pulse generator 101 senses a change of operation, the pulse generator 101 can record the values provided by other sensors. For example, the pulse generator 101 can record an indication of the current body position and/or orientation of the patient with a gyroscopic sensor to determine whether the patient is standing or lying down. The pulse generator 101 can sense the patient's current activity level with an accelerometer to determine a change in the movement of the patient and/or can sense the patient's blood pressure, thoracic impedance, and/or other suitable physiological indicators.

Based on the foregoing recorded measurements, the pulse generator 101 can establish the patient preferences. The pulse generator 101 can correlate at least one of the patient's indicated changes, the output of the pulse generator 101, with at least one of the current body position, the current activity level, and/or other physiological indicators of the patient. For example, in a particular embodiment, the pulse generator 101 can correlate the amplitude of the applied therapy signals with a patient's body position in two dimensions to generate a first preferred amplitude for the stimulation parameters when the patient is standing and a second preferred amplitude when the patient is lying down. In certain embodiments, each of the preferred amplitudes can be an arithmetic mean of multiple measurements corresponding to each body position, respectively. In other embodiments, the preferred amplitudes can be a median value, a geometric median value, a harmonic mean, a quadratic mean, a weighted mean (e.g., based on time of a day), and/or other values derived from the measurements.

In further embodiments, the pulse generator 101 can correlate several parameters of the applied stimulation parameters with the patient status in three, four, five, and/or other numbers of sensor inputs, which may correspond to patient activity levels, physiological parameters, and/or other suitable parameters. For example, the pulse generator 101 can correlate the stimulation parameters with certain values of both the body position and the activity level of the patient. As a result, the pulse generator 101 may calculate the preferred amplitude values as shown in the following table:

|  | Position | Activity level |
| --- | --- | --- |
| First selected (e.g., preferred) amplitude | Standing | Mobile |
| Second selected (e.g., preferred) amplitude | Standing | Immobile |
| Third selected (e.g., preferred) amplitude | Lying down | Immobile |

Even though particular values of the patient's position and activity level are used in the above example, in other examples, the pulse generator 101 can use other values of the patient's position (e.g., sitting) and/or activity level (e.g., walking, running, etc.). In yet further embodiments, the pulse generator 101 can use other patient parameters (e.g. thoracic impedance, heart rate, etc).

In certain embodiments, the initial (learning) period can be a predetermined time period (e.g., 2-5 weeks) set by the caregiver. In other embodiments, the initial period can be determined by the measurements recorded and stored in the pulse generator 101. For example, the initial period can expire when the derived first and second preferred amplitudes have reached a confidence level of at least 80% or another suitable value. In further embodiments, the patient and/or the caregiver can terminate the initial period irrespective of an elapsed time or the current confidence level of the first and second preferred amplitudes and reset the pulse generator 101 with most recent parameters and/or other suitable parameters.

Once the patient preferences are established (e.g., once the learning phase is complete), the pulse generator 101 can automatically adjust the stimulation parameters based on the sensed measurements. For example, when the pulse generator 101 receives an indication that the patient is currently standing, the pulse generator 101 can automatically adjust the stimulation parameters (e.g., an amplitude) based on a corresponding value of the preferred amplitude in the database for the standing position. The patient does not have to manually operate the remote control 105 in order to adjust the applied stimulation parameters. As a result, several embodiments of the therapy system 100 are less cumbersome, time-consuming, and/or restrictive to operate than are conventional techniques.

After the initial period expires, the pulse generator 101 can continue recording adjustment inputs from the patient regarding the operating parameters of the pulse generator 101, the current values of the generated stimulation parameters, and/or the current status of the patient as described above. The pulse generator 101 can periodically (e.g., weekly, biweekly, etc.) or continuously update (e.g., refine) the patient preferences based on these newly recorded measurements. In other embodiments, the process of further updating the preferences can be omitted.

In yet further embodiments, if the pulse generator 101 detects a large change in the patient's status, the pulse generator 101 can output an alarm to the patient and/or the caregiver indicating that an additional assessment is needed. In other examples, the patient and/or the caregiver can decide when to reestablish patient preferences.

Several embodiments of the therapy system 100 can improve treatment efficiency for the patient. Instead of estimating the applied therapy signals for each patient status, several embodiments of the therapy system 100 allow customization of the applied therapy signals based on previous measurements of the applied therapy signals, thus improving the efficacy of the treatment and/or reducing or eliminating the need for the patient to manually adjust stimulation settings. In certain embodiments, the therapy system 100 can also provide multiple stimulation levels to individually correspond to different patient statuses measured by the sensing element 126. For example, if the sensing element 126 indicates that the patient's motion exceeds a first threshold, a first stimulation level may be used. If the patient's motion exceeds a second threshold greater than the first threshold, a second stimulation level may be used. The caregiver and/or the patient may select any desired number of stimulation levels and/or thresholds of patient status.

Even though the therapy system 100 is described above as establishing the patient preferences via the implanted pulse generator 101, in other embodiments, this function can be performed with additional support from other devices. For example, the pulse generator 101 can transfer the recorded measurements to the optional personal computer 110 and/or the network server 114, and the personal computer 110 and/or the network server 114 can establish the patient preferences. In yet further embodiments, the patient may establish additional programs for the pulse generator 101, and the caregiver may have override capability over these additional programs.

Figure 2:
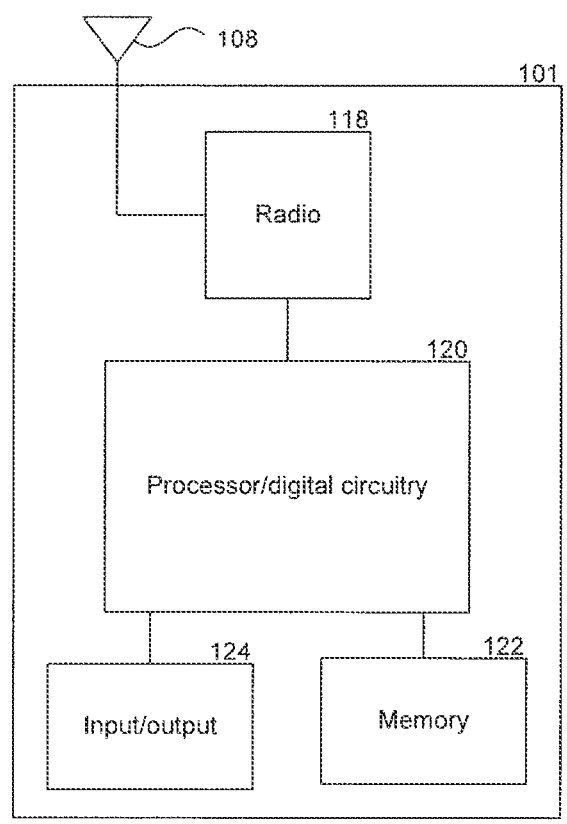
FIG. 2 is a functional block diagram illustrating logic components of a pulse generator suitable for use in the therapy system of FIG. 1 in accordance with embodiments of the present disclosure.

FIG. 2 is a functional block diagram illustrating components of the pulse generator 101 of FIG. 1 in accordance with embodiments of the disclosure. As shown in FIG. 2, the pulse generator 101 can include a radio 118 coupled to an antenna 108, and a processor 120 coupled to an input/output component 124 and a memory 122. In other embodiments, the pulse generator 101 can also include a battery, a power management circuit, or other suitable electronic and/or mechanical components.

The radio 118 can include a frequency modulator, an amplitude modulator, and/or other suitable circuitry for modulating inductive protocols. The processor 120 is configured to provide control signals to and receive data from the radio 118. In certain embodiments, the processor 120 can include a microprocessor, a field-programmable gate array, and/or other suitable logic components. In other embodiments, the processor 120 may also include a detector or a decoder with associated software and/or firmware to perform detection/decoding functions and process received signals. The memory 122 can include volatile and/or non-volatile media (e.g., ROM, RAM, magnetic disk storage media, optical storage media, flash memory devices, and/or other suitable storage media). The memory 122 can be configured to store data received from, as well as instructions for, the processor 120. The input/output component 124 can include logic components (e.g., a MODEM driver) that receive and interpret input from the remote control 105 (FIG. 1) as well as hardware components (e.g., a vibrator) that output information to the patient.

Figure 3:
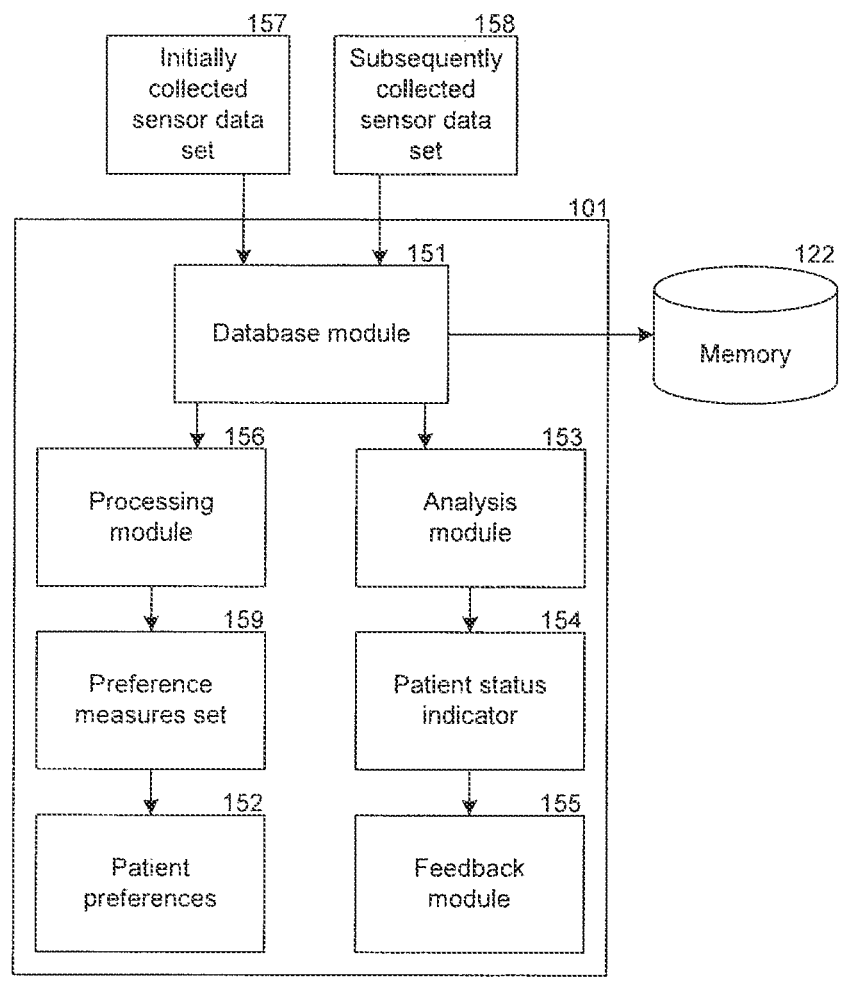
FIG. 3 is a block diagram illustrating software modules of the pulse generator in FIG. 2 in accordance with embodiments of the present disclosure.

FIG. 3 is a block diagram showing software modules of the pulse generator 101 of FIG. 2. Each module is a computer program written as source code in a conventional programming language (e.g., the C++ or Java programming languages) and is presented for execution by a CPU of the pulse generator 101 as object or byte codes. The various implementations of the source code and object and byte codes can be held on a computer-readable storage medium such as the memory 122.

As shown FIG. 3, the pulse generator 101 can include three basic software modules, which functionally define the primary operations performed by the pulse generator 101: a database module 151, an analysis module 153, and a processing module 156. In the described embodiment, the processor 120 executes all of these modules in the pulse generator 101. However, in other embodiments, these modules can also be executed in a distributed computing environment. The module functions are further described below beginning with reference to FIGS. 5 and 6.

As described above, the patient preferences are established during the initial or learning period. The pulse generator 101 receives an initially collected sensor data set 157 representing patient measurements collected from the implantable pulse generator 101 (FIG. 1) during the initial period, as discussed in more detail below with reference to FIG. 5. The initially collected sensor data set 157 can be forwarded to the database module 151 for storage in the patient records, located at the memory 122. During subsequent, on-going monitoring of the patient status, the pulse generator 101 periodically records a subsequently collected sensor data set 158, which is also forwarded to the database module 151 for storage.

The database module 151 is configured to organize the individual patient records stored in the memory 122 and provide the facilities for efficiently storing and accessing the collected sensor data sets 157 and 158 and patient data maintained in those records. Examples of suitable database schemes for storing the collected sensor data sets 157 and 158 in a patient record are described below with reference to FIG. 4. Any of a variety of suitable database organizations can be utilized, including a flat file system, hierarchical database, relational database, or distributed database, such as those provided by database vendors, including Oracle Corporation of Redwood Shores, Calif.

The processing module 156 processes the initially collected sensor data set 157 stored in the patient records to produce the patient preferences 152. The patient preferences 152 include a set of preference measurements 159 (e.g., body positions, the gross time of day, and/or other suitable sensor readings), which can be either directly measured or indirectly derived from patient information. The patient preferences 152 can be used to adjust the operating parameters for the pulse generator 101 and to monitor patient status on a continuous, ongoing basis.

On a periodic basis (or as needed or requested), the processing module 156 reassesses and updates the patient preferences 152. The database module 151 can receive the subsequently collected sensor data set 158 from the pulse generator 101 (FIG. 1) subsequent to the initial period. The processing module 156 re-assimilates the additional collected data set into new patient preferences 152. The operations performed by the processing module 156 are described in more detail below with reference to FIGS. 5 and 6.

The analysis module 153 analyzes the subsequently collected sensor data set 158 stored in the patient records in the memory 122. The analysis module 153 monitors patient status and makes an automated determination in the form of a patient status indicator 154. Subsequently collected sensor data sets 158 are periodically received from pulse generator 101 and maintained by the database module 151 in the memory 122. Through the use of this collected information, the analysis module 153 can continuously follow the patient status and can recognize any trends in the collected information that might warrant medical intervention. The analytic operations performed by the analysis module 153 are described in more detail below with reference to FIGS. 5 and 6. The feedback module 155 can provide feedback to the patient based, at least in part, on the patient status indicator 154. For example, the feedback module 155 may cause the pulse generator 101 to vibrate, to beep, and/or to output a warning message on the display 107 of the remote control 105 (FIG. 1).

Figure 4:
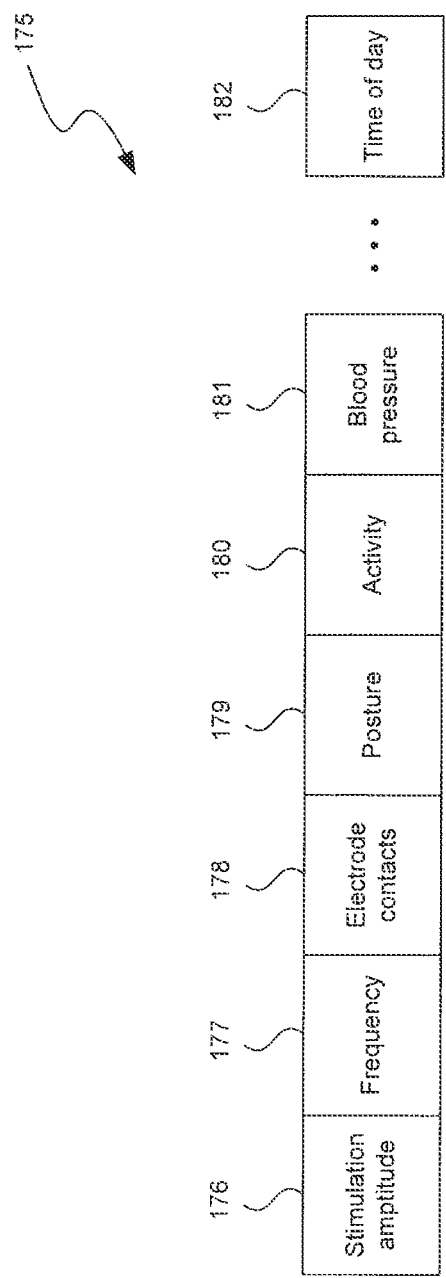
FIG. 4 is a database schema illustrating an organization of a treatment profile in accordance with embodiments of the present disclosure.

FIG. 4 is a database schema illustrating an organization of a patient preference record 175 stored as a part of a patient record in the memory 122 of the pulse generator 101 of FIG. 2. The patient preference record 175 corresponds to the patient preferences 152 (FIG. 3). In the illustrated embodiment, only the information pertaining to the set of preference measurements in the patient preferences 152 are shown for purposes of clarity. For example, as shown in FIG. 4, the patient preference record 175 can include the following information: stimulation amplitude 176, frequency 177, electrode contact information 178, posture 179, activity level 180, blood pressure 181, and time of day 182. In other embodiments, the patient preference record 175 can also include patient profile information, historical data, and/or other pertinent data (not shown). During the initial (learning) phase, multiple preferences 175 are collected for corresponding combinations of the foregoing parameters.

Figure 5:
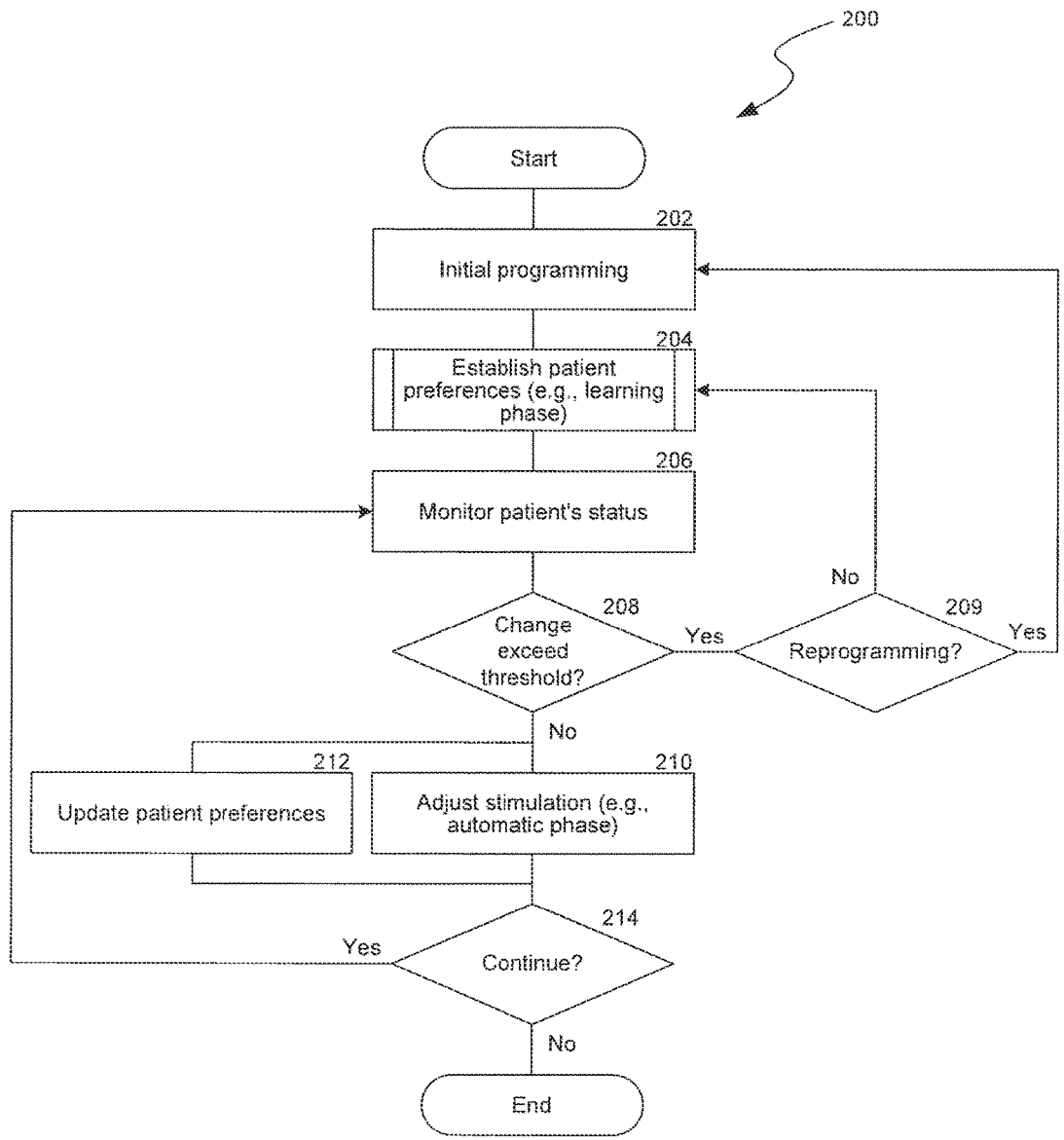
FIG. 5 is a flow diagram illustrating a method for stimulating and blocking neuronal tissues in accordance with embodiments of the present disclosure.

FIG. 5 is a flow diagram showing a method 200 for providing signals (e.g., blocking signals) to neuronal tissues in accordance with an embodiment of the present disclosure. In the illustrated embodiment, the method 200 can include two phases: (1) collecting data and processing patient preferences (e.g., in a learning phase, block 204), and (2) automatically applying stimulation based on the patient preferences, including updating the preferences as needed (block 210). The method 200 can be implemented as a conventional computer program for execution by the pulse generator 101 (FIG. 1). Even though the method 200 is described below with reference to the therapy system 100 of FIG. 1, the method 200 can also be practiced in other suitable systems for stimulating neuronal tissues.

As shown in FIG. 5, the method 200 can include programming the pulse generator 101 (FIG. 1) with an initial set of operating parameters (block 202). The initial set of operating parameters can include a plurality of programs corresponding to various patient statuses. For example, the initial set of operating parameters may include a first program corresponding to the patient standing and a second program corresponding to the patient lying down. The first and second programs can individually include an amplitude, a frequency, an electrode contact arrangement, and/or other suitable operating parameters for providing the therapy signals to the patient. In certain embodiments, the programs are customizable. For example, the caregiver and/or the patient may create additional programs and/or modify existing programs to suit a particular need.

The method 200 can also include establishing a preference or profile for the patient during an initial period (block 204) e.g., during a learning phase. The preference can include preference values for the operating parameters derived from recorded values for a particular patient status. For example, the preference may include a first preferred value for the stimulation amplitude when the patient is standing and a second preferred value when the patient is lying down. The preferences may also include baseline blood pressure, thoracic impedance, and/or other physiological indicators that give information about the patient status. Details of establishing the patient preferences are described in more detail below with reference to FIG. 6.

The method 200 can further include using the data from the patient preferences to automatically adjust the therapy applied to patient, e.g., during an automated operation phase. This phase can include monitoring a patient status (block 206). In one embodiment, monitoring a patient status includes determining the current body position of the patient with a gyroscope and indicating whether the patient is standing or lying down. In other embodiments, monitoring a patient status can also include sensing the patient's current activity level, e.g., with an accelerometer. In further embodiments, monitoring a patient status can include measuring the blood pressure, and/or other suitable physiological parameters of the patient. In yet further embodiments, monitoring a patient status can include accepting a patient input using, for example, the remote control 105. Although such an input may not be required of the patient in light of the automatic operation of the system, the system can receive patient inputs that may override or facilitate the automatic operation.

The method 200 can also include determining whether a change in the patient status has exceeded a preset threshold (block 208), e.g., the delta threshold change, described previously. For example, the determination can be based on determining whether a subsequent measurement (e.g., lead impedance) exceeds a baseline value for a particular patient status (e.g., standing) by a certain percentage (e.g., 20%) or a preselected value (e.g., 4000 ohms). In other examples, the determination can also be based on other suitable criteria. The determination can be performed weekly, bi-weekly, at other periodic intervals, or on an as needed basis.

If the change in the patient status exceeds the preset threshold, the method 200 includes determining whether reprogramming is necessary (block 209). In one embodiment, the pulse generator 101 can provide a warning signal to the patient indicating that the caregiver should perform a checkup. The caregiver can then determine whether the signal delivery device 114 (FIG. 1) requires any physical adjustment. If so, then the caregiver may readjust the signal delivery device 114, and the process may revert to the initial programming stage at block 202. If not, the process can revert to establishing the patient preferences at block 204 and purging or overwriting at least a portion of the existing patient preferences.

If the change in the patient status does not exceed the preset threshold, the method 200 can adjust the stimulation based on the measured patient status and the preferences in a closed-loop fashion (block 210). In one embodiment, adjusting the stimulation can include selecting a setpoint for an operating parameter (e.g., the stimulation amplitude) of the pulse generator 101 based on the preference value for a particular patient status. For example, the setpoint for the stimulation amplitude can be set to the preferred value or can be offset by a bias factor selected by the patient and/or the caregiver. In other embodiments, adjusting the stimulation can also include accepting input from the patient for increasing or decreasing the current stimulation level. In any of these embodiments, block 210 can include directing a change in the stimulation applied to the patient, based on the preference established in block 204.

The method 200 can also include updating the preferences after the initial period (block 212). For example, updating the preferences can include re-assimilating subsequent measurements for the patient status and/or values of the therapy signals. The method 200 can further include determining whether the process should continue (block 214). If so, the process reverts to monitoring the patient status at block 206. If not, the process ends. The updating can be performed weekly, bi-weekly, in other periodic intervals, or continuously.

Figure 6:
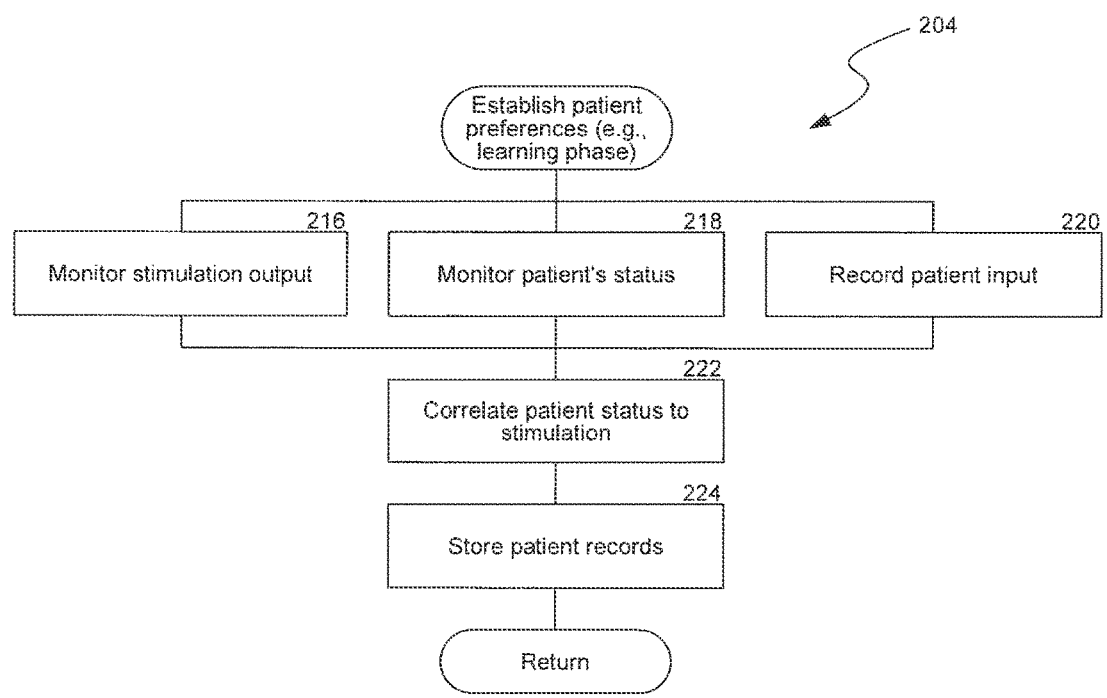
FIG. 6 is a flow diagram illustrating a method for establishing patient preferences during a learning phase in accordance with embodiments of the present disclosure.

FIG. 6 is a flow diagram showing a method 204 for establishing patient preferences in accordance with an embodiment of the present disclosure, e.g., during the learning phase described above. As shown in FIG. 6, the method 204 can include at least one of monitoring the stimulation output from the pulse generator 101 (block 216), monitoring a patient status (block 218), and recording a patient input (block 220). The method 204 can also include correlating the monitored patient status to the monitored stimulation output (block 222). The stimulation output can be categorized based on readings from the sensing element 126. In one example, the stimulation output can be categorized based on whether a gyroscopic reading from the sensing element 126 exceeds a predetermined threshold indicating the patient is standing, or below the predetermined threshold indicating the patient is lying down. The stimulation output corresponding to the patient as standing (or lying down) can then be calculated to derive the preference value for the particular patient status. In other examples, multiple thresholds and/or patient position values corresponding to the thresholds may be used. In further examples, the stimulation output can be categorized based on other suitable patient statuses. The method 204 can further include storing the correlated patient measurements as patient records (block 224) as shown in FIG. 4 in the memory 122 (FIG. 2) of the pulse generator 101.

The learning phase and/or the automatic operation phase can have other characteristics and/or other interrelationships in other embodiments. For example, in one such embodiment, the method 200 can include prioritizing the patient's preferences during the learning phase and storing this information for later use. In a particular example, the method 200 can include ordering the patient preferences by the frequency with which each preference is requested by the patient, and/or the duration that the preferred parameter value is in use. If the patient chooses "Program 4" most often when lying down, but then chooses "Program 2," "Program 3" and "Program 1" in descending order, the method can include storing this information. Later (e.g., during the automatic operation phase), if the patient manually overrides the now-default selection of "Program 4," the method can include presenting the patient with a preference-ordered list of next-best options, based on the information gathered during the learning phase. The options can be presented in a variety of suitable manners, including a textual list or a graphical representation. Accordingly, if the patient becomes dissatisfied with the program selected as a result of the learning phase, the method can automatically provide likely backup program selections, without requiring the patient to reconsider every possible program as an option. This can allow the patient to more quickly zero in on an effective new program if the existing program becomes less satisfactory, which may result e.g., if the implanted lead shifts or migrates.

In another embodiment, the method 200 can implement the foregoing preference tracking without necessarily making a clear distinction between a learning phase and an operation phase. Instead, both phases can be executed simultaneously. For example, the method 200 can include tracking patient preferences for a sliding period of time (e.g., one week or two weeks), and continuously updating the signal delivery parameters and patient prioritization of programs. When the patient manually overrides the automatically delivered program, the method can provide a prioritized list of alternate programs, as discussed above. The list can be weighted by the frequency with which each program is selected and/or the duration each program is in use, as discussed above. In other embodiments, the list can be weighted in other manners. For example, the most recent patient selection can receive the highest priority.

In still further embodiments, the foregoing meshed learning/operation phases can be implemented without tracking a prioritized list of patient preferences. Instead, the method can include continuously updating the applied signal delivery parameters based on feedback collected over a period of time (e.g., the past week, two weeks, or other period). If the patient does not frequently provide manual input or feedback, the signal delivery parameters can remain generally static. If the patient frequently updates the parameters, the method can adjust the signal delivery parameters accordingly, using an appropriate weighting scheme (e.g., greater weight given to the most recent patient request).

Figure 7A:
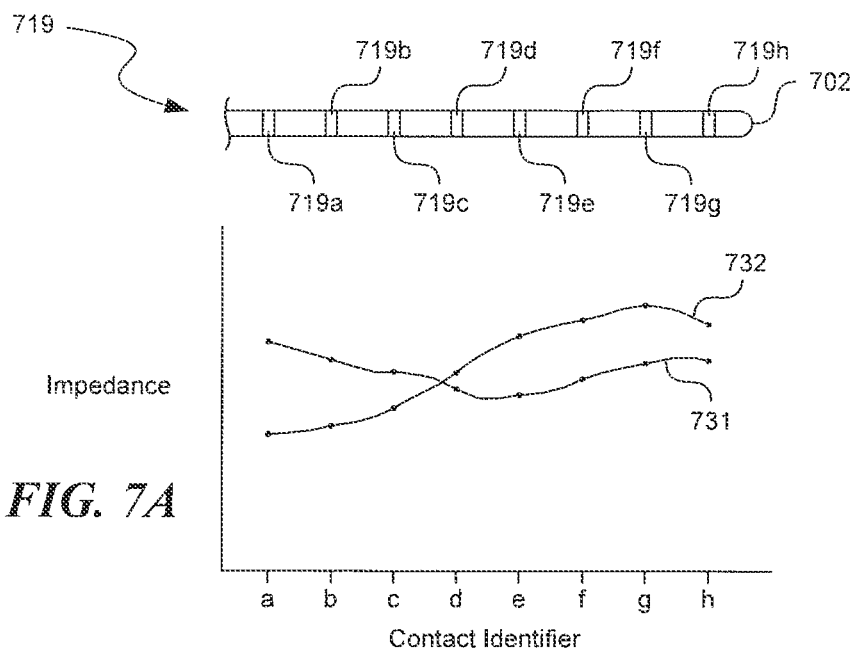
FIGS. 7A-7C graphically illustrate impedance characteristics that may be correlated with patient state in accordance with further embodiments of the present disclosure.
Figure 7B:
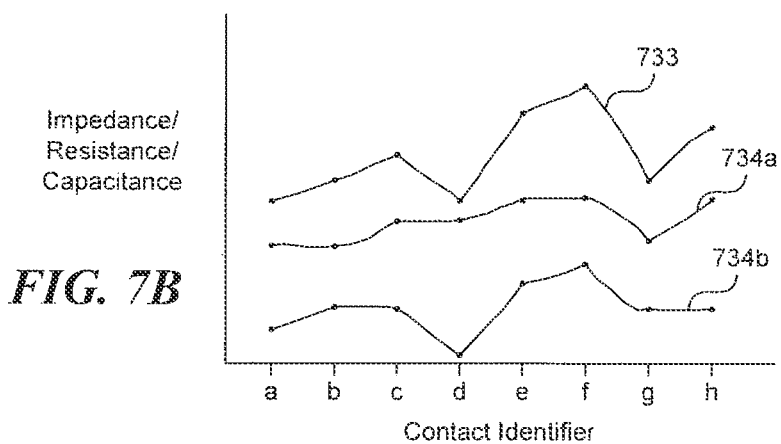
Figure 7C:
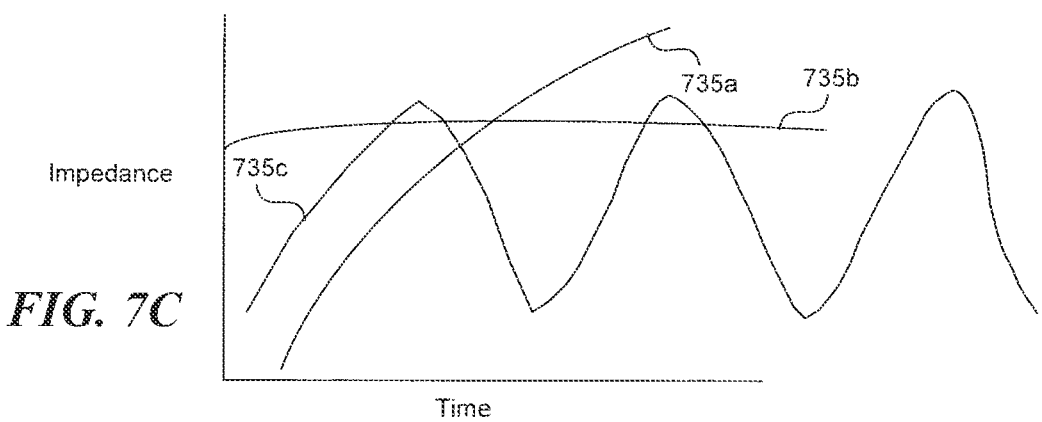

As described above, one or more impedance sensors can be used during the learning phase to correlate patient status (e.g., patient posture and/or activity level) with the patient's preferred stimulation parameters (e.g., therapy signal strength). The same impedance sensor or sensors can subsequently be used to identify changes in patient state, in response to which the system can automatically adjust the operating parameters with which the therapeutic signals are applied. FIGS. 7A-7C graphically illustrate representative embodiments in accordance with which impedance information may be used to control system operation.

Beginning with FIG. 7A, the patient may be implanted with a lead 702 having multiple contacts 719 (illustrated as first-eighth contacts 719a-719h) arranged along a lengthwise axis of the lead 702. Particular contacts 719 or combinations of contacts 719 form part of a therapy delivery circuit, which also includes the patient's tissue, and via which the stimulation signals provide a therapeutic effect to the patient. In addition to facilitating delivery of the therapeutic signals, the circuit (e.g., the impedance of the circuit) can be used to identify patient status and/or changes in the patient status. In a particular example shown in FIG. 7A, circuit impedance is plotted as a function of the contact identifier (a, b, c h) for multiple patient postures. When the patient assumes a first posture, the impedance can be characterized by a first impedance profile 731, and when the patient assumes a second posture different than the first posture, the impedance can be characterized by a second impedance profile 732. During the learning phase, the system can correlate patient preferred stimulation parameters with patient posture, as identified by the profiles 731 and 732. During the automatic operation phase, the system can identify a patient posture by matching, approximately matching, or otherwise linking measured impedance profiles with profiles obtained and stored during the learning phase. The system can then automatically apply patient-preferred signal strengths to each of the contacts 719a-719h (or subsets of contacts) in a manner that corresponds to the preferred values established during the learning phase. The foregoing arrangement can be used for any number of postures, positions, and/or other patient states in accordance with a variety of embodiments of the disclosure.

FIG. 7B illustrates an overall impedance profile 733 as a function of contact identifier, at a particular point in time for a particular patient position. As shown in FIG. 7B, the overall impedance profile 733 includes a capacitive component 734a and a resistive component 734b. Each of these components may have different values depending upon the particular location along the lead 702 (FIG. 7A) at which the impedance is detected or estimated. This information can be used, alone or in conjunction with other information, to identify patient status. For example, the resistance and/or capacitance associated with a particular contact may be a function of the proximity of the contact to the patient's soft tissue, bone structure, and/or cerebral spinal fluid. In a particular example, the resistive component 734b of the overall impedance profile 733 may have a shape different than the capacitive component 734a, as shown in FIG. 7B, depending upon factors that include the nature of the adjacent tissue. Accordingly, the system can correlate the capacitive and resistive profiles, and/or differences between the capacitive and resistive profiles to identify patient status, such as patient posture. In one example, the impedance profile shown in FIG. 7B may correspond to the patient standing, as opposed to sitting. The impedance profile can have other shapes, depending upon the location and orientation of the lead 702 within the patient's body. In any of these embodiments, during the learning phase, the system can correlate patient preferences with capacitive and/or resistive profiles, and/or differences between the profiles, with different profiles corresponding to different patient statuses. After the learning phase has been completed, the system can automatically implement patient-preferred stimulation parameters based on the profiles determined from impedance inputs received from the lead 702.

In still further embodiments, the impedance (e.g., overall impedance, resistance, and/or capacitance) can also be tracked as a function of time to identify patient status. For example, FIG. 7C illustrates impedance as a function of time for a representative one of the contacts 719 shown in FIG. 7A. Line 735a indicates the impedance changing at a moderate rate, which may indicate that the patient is gradually moving from one position to another (e.g., bending). Line 735b may be correlated with a relatively slow or zero change in patient position, which can correspond to a different activity undertaken by the patient (e.g., sleeping). Line 735c indicates that the patient is rapidly changing posture in a cyclic manner, which can correspond to yet another patient activity (e.g., walking, running or jumping). The rate of change of the impedance function can be determined using suitable differentiation or other slope-determining techniques. The system can automatically correlate patient preferences with the status information identified by the impedance characteristics shown in FIG. 7C during a learning phase, and can then automatically implement the patient preferences during an automatic operation phase, based on impedance characteristics received from the lead 702.

In particular embodiments described above, the impedance characteristics are identified via contacts that also provide the therapy signal. The impedance characteristics can be determined from a therapy signal, or from a separate signal applied to the therapy contacts. In other embodiments, contacts that are not concurrently providing therapy, and/or other contacts (e.g., dedicated sensors), can be used to identify appropriate impedance values. Representative techniques for detecting impedance via implanted leads are disclosed in U.S. application Ser. No. 12/499,769, filed on Jul. 8, 2009 and incorporated herein by reference. In other embodiments, impedance measurements can be used in manners other than those described above. For example, the patient may have multiple leads or other arrangements in which impedance sensors are remote from each other, and the impedance profile information can be collected from the multiple leads/sensors. Profiles may be stored in a lookup table, profile bank or other suitable storage medium. The patient status can correspond to positions and/or activities other than those described above e.g., squatting, lying down on the patient's left side, lying down on the patient's right side, among others. In still further embodiments, the foregoing impedance profile information may be used in contexts other than spinal cord stimulation, e.g., peripheral nerve stimulation therapy, or cardiac therapy.

Several embodiments of the systems and methods described above with reference to FIGS. 7A-7C were described in the context of profiles associated with a single longitudinally-extending lead. In other embodiments, the profiles can be established for axes other than a longitudinal axis, and/or for multiple axes. For example, the electrode array 103 shown in FIG. 1, and/or an arrangement of multiple leads placed side-by-side, can be used to establish lateral profiles or a two-dimensional map of impedance information.

Several embodiments of the methods discussed above can improve patient comfort by allowing customization of the applied therapy signals. For example, the customization can include generating patient preferences based on previous measurements of the patient's preferences. The patient's comfort is further enhanced because several embodiments of the methods include detecting the patient's status and automatically adjusting a stimulation level of the applied therapy signals based on the patient preferences without patient input. The foregoing arrangement can reduce patient workload by automatically tracking the patient's stimulation preferences and automatically adjusting the applied stimulation parameters accordingly. In at least some embodiments, the process of adjusting the applied stimulation parameters based on patient preferences is performed at the patient's implanted device. This arrangement can reduce or eliminate the need for the patient to interact with any device other than the implant and the patient programmer.

From the foregoing, it will be appreciated that specific embodiments of the disclosure have been described herein for purposes of illustration, but that various modifications may be made without deviating from the disclosure. For example, in certain embodiments, the pulse generator 101 can include a plurality of integrated and remote sensing elements. Certain aspects of the disclosure described in the context of particular embodiments may be combined or eliminated in other embodiments. For example, in certain embodiments, the remote control 105 may be omitted, and the personal computer 110 may be operatively coupled to the antenna 108 for communicating with the pulse generator 101. Further, while advantages associated with certain embodiments have been described in the context of those embodiments, other embodiments may also exhibit such advantages, and not all embodiments need necessarily exhibit such advantages to fall within the scope of the disclosure. Accordingly, the invention can include other embodiments not explicitly described or shown herein.

We claim:

1. A computer-implemented method for automatically adjusting stimulation delivered to a patient, the method comprising:
   generating an ordered listing of patient preferences for stimulation parameters based at least in part on a duration of use of individual patient preferences;
   delivering an electrical therapy signal to the patient via an implantable signal delivery device, in accordance with a first set of stimulation parameters having a first ranking in the ordered listing; and in response to an input, automatically delivering the electrical therapy signal in accordance with a second set of stimulation parameters having a second ranking lower than the first ranking.

2. The method of claim 1 wherein generating the ordered listing is further based at least in part on a frequency of requests by the patient for individual patient preferences.

3. The method of claim 1, further comprising:
establishing a preference baseline including the patient preferences,
wherein the patient preferences have patient preferred values of the stimulation parameters, and
wherein the ordered listing is a ranked listing according to the patient preferred values.

4. The method of claim 1 wherein delivering the electrical therapy to the patient includes delivering the electrical therapy to a spinal cord region of the patient.

5. The method of claim 1 wherein the input corresponds to an override input of the delivered electrical therapy signal, wherein the override input is provided by the patient.

6. The method of claim 1 wherein the input corresponds to a change in a value of a particular patient status, wherein the value is an impedance value measured via the implantable signal delivery device.

7. The method of claim 6 wherein the change in the value of the particular patient status corresponds to the impedance value falling below or exceeding a threshold value.

8. The method of claim 1 wherein the first set of stimulation parameters includes an identity of a first contact of the signal delivery device, and wherein the second set of stimulation parameters includes an identity of a second contact of the signal delivery device.

9. The method of claim 8 wherein the first contact is positioned to deliver the electrical therapy signal having the first set of stimulation parameters to treat a first pain area, and wherein the second contact is positioned to deliver the electrical therapy signal having the second set of stimulation parameters to treat a second pain area.

10. The method of claim 1 wherein the first set of stimulation parameters includes a first amplitude, and wherein the second set of stimulation parameters includes a second amplitude different than the first amplitude.

11. A therapy system for treating a patient, the system comprising:
a signal delivery device having a plurality of contacts; and
an implantable pulse generator electrically coupleable to the signal delivery device to apply therapy signals to the patient, wherein the implantable pulse generator includes a computer-readable medium containing instructions that, when executed, cause the therapy system to:
generate an ordered listing of patient preferences for stimulation parameters based on at least one of (a) a frequency of requests by the patient for individual patient preferences, or (b) a duration of use of the individual patient preferences;
deliver an electrical therapy signal to the patient, via the signal delivery device, with a first set of stimulation parameters, wherein the first set of stimulation parameters has a first ranking in the ordered listing; and
in response to an input, automatically adjust the electrical therapy signal in accordance with a second set of stimulation parameters having a second ranking lower than the first ranking.

12. The system of claim 11 wherein the input corresponds to a change in value of a particular patient status, and wherein the value is an impedance value measured via the signal delivery device.

13. The system of claim 11 wherein the instructions, when executed, further cause the therapy system to:
establish a preference baseline including the patient preferences,
wherein the patient preferences have patient preferred values of the stimulation parameters correlated with corresponding values of patient status, and
wherein the ordered listing is a ranked listing according to the patient preferred values.

14. The system of claim 11 wherein delivering the electrical therapy to the patient includes delivering the electrical therapy to a spinal cord region of the patient, and wherein the first set of stimulation parameters includes an identity of a first contact of the signal delivery device, and the second set of stimulation parameters includes an identity of a second contact of the signal delivery device, the first and second contacts being positioned to treat lower back pain.

15. A computer-implemented method for automatically adjusting stimulation delivered to a patient, the method comprising:
establishing a preference baseline including an ordered listing of patient preferences, wherein the patient preferences have patient-preferred values of stimulation parameters correlated with corresponding values of patient status;
delivering an electrical therapy signal, via an implantable signal delivery device, in accordance with a first set of stimulation parameters, wherein the first set of stimulation parameters is based on the preference baseline and has a first ranking on the ordered listing;
monitoring a value of a particular patient status;
in response to an input and a change in the value of the particular patient status, automatically delivering the electrical therapy signal in accordance with a second set of stimulation parameters having a second ranking lower than the first ranking,
wherein the input is provided by the patient and is an override of the delivery of the electrical therapy signal having the first set of stimulation parameters.

16. The computer-implemented method of claim further comprising:
prior to delivering the electrical therapy signal in accordance with the second set of stimulation parameters, presenting at least a portion of the ordered listing to the patient.

17. The computer-implemented method of claim 15 wherein monitoring the value of the particular patient status includes measuring an impedance value via the implantable signal delivery device, and wherein the change in the value corresponds to the impedance value falling below of exceeding a threshold value.

18. A computer-implemented method for automatically adjusting stimulation delivered to a patient, the method comprising:
generating an ordered listing of patient preferences for stimulation parameters;
delivering an electrical therapy signal to the patient via an implantable signal delivery device, in accordance with a first set of stimulation parameters having a first ranking in the ordered listing; and
in response to an input, automatically delivering the electrical therapy signal in accordance with a second set of stimulation parameters having a second ranking lower than the first ranking, wherein the input corresponds to an override input of the delivered electrical therapy signal, and wherein the override input is provided by the patient.

19. A computer-implemented method for adjusting stimulation delivered to a patient, the method comprising:

generating an ordered listing of patient preferences for stimulation parameters based on at least one of (a) a frequency of requests by the patient for individual patient preferences, or (b) a duration of use of the individual patient preferences;

delivering an electrical therapy signal to the patient via an implantable signal delivery device, in accordance with a first set of stimulation parameters having a first ranking in the ordered listing; and in response to an input, delivering the electrical therapy signal in accordance with a second set of stimulation parameters having a second ranking lower than the first ranking.

20. The computer-implemented method of claim 19 wherein generating an ordered listing of patient preferences for stimulation parameters is based on the frequency of requests by the patient for individual patient preferences.

21. The computer-implemented method of claim 19 wherein generating an ordered listing of patient preferences for stimulation parameters is based on the duration of use of the individual patient preferences.

* * * * *